(12) United States Patent
Kruip (10) Patent No.: US 8,838,202 B2
(45) Date of Patent: Sep. 16, 2014

(54) PARTICLE RADIATION THERAPY EQUIPMENT

(75) Inventor: Marcel Jan Marie Kruip, Oxford (GB)

(73) Assignee: Siemens Plc, Frimley, Camberley, Surrey (GB)

( * ) Notice: Subject to any disclaimer, the term of this patent is extended or adjusted under 35 U.S.C. 154(b) by 1787 days.

(21) Appl. No.: 11/917,959

(22) PCT Filed: Jun. 16, 2006

(86) PCT No.: PCT/GB2006/050159
§ 371 (c)(1),
(2), (4) Date: Dec. 18, 2007

(87) PCT Pub. No.: WO2006/136864
PCT Pub. Date: Dec. 28, 2006

(65) Prior Publication Data
US 2009/0234219 A1 Sep. 17, 2009

(30) Foreign Application Priority Data

Jun. 22, 2005 (GB) .................................. 0512719.6

(51) Int. Cl.
*A61B 5/05* (2006.01)
*G01R 33/381* (2006.01)
*A61N 5/10* (2006.01)

(52) U.S. Cl.
CPC .............. *G01R 33/381* (2013.01); *A61N 5/1067* (2013.01); *A61N 2005/1055* (2013.01); *A61N 2005/1087* (2013.01); *A61N 5/1049* (2013.01)
USPC .............................. 600/411; 335/296; 335/299

(58) Field of Classification Search
None
See application file for complete search history.

(56) References Cited

U.S. PATENT DOCUMENTS

| | | | | |
|---|---|---|---|---|
| 4,728,896 A | * | 3/1988 | Bendall et al. | 324/318 |
| 5,162,768 A | * | 11/1992 | McDougall et al. | 335/296 |
| 5,917,395 A | | 6/1999 | Overweg | |
| 6,147,578 A | * | 11/2000 | Panfil et al. | 335/296 |
| 6,198,957 B1 | * | 3/2001 | Green | 600/411 |
| 6,950,001 B2 | * | 9/2005 | Kruip et al. | 335/296 |
| 7,167,004 B1 | * | 1/2007 | Kruip | 324/320 |

(Continued)

FOREIGN PATENT DOCUMENTS

| | | |
|---|---|---|
| CN | 1489700 A | 4/2004 |
| CN | 1589729 A | 3/2005 |

(Continued)

OTHER PUBLICATIONS

Chinese Office Action dated Sep. 25, 2009 (ten (10) pages).

(Continued)

*Primary Examiner* — Nicholas Evoy
(74) *Attorney, Agent, or Firm* — Crowell & Moring LLP (57) ABSTRACT

Particle radiation therapy equipment arranged to apply a charged particle beam to a region of application in a predetermined direction, comprising a charged particle beam source arranged to direct a charged particle beam in the predetermined direction, further comprising magnetic field generation means for generating a magnetic field in an imaging volume which includes the region of application at the same time that the charged particle beam is applied, wherein the magnetic field generation means is arranged to provide access to the region of application for the charged particle beam, and to provide a homogeneous magnetic field in the region of application of the charged particle beam, said magnetic field being directed substantially in the predetermined direction.

11 Claims, 5 Drawing Sheets

(56) References Cited

U.S. PATENT DOCUMENTS

| | | | |
|---|---|---|---|
| 7,173,507 B2 | 2/2007 | Ries | |
| 7,960,710 B2* | 6/2011 | Kruip et al. | 250/492.3 |
| 8,427,148 B2* | 4/2013 | O'Connor | 324/307 |
| 8,554,302 B2* | 10/2013 | Gross et al. | 600/411 |
| 2004/0199068 A1* | 10/2004 | Bucholz et al. | 600/411 |
| 2008/0208036 A1* | 8/2008 | Amies et al. | 600/411 |
| 2009/0124887 A1* | 5/2009 | Roell et al. | 600/411 |
| 2009/0149735 A1* | 6/2009 | Fallone et al. | 600/411 |
| 2010/0013418 A1* | 1/2010 | Kruip et al. | 315/501 |
| 2010/0265018 A1* | 10/2010 | Kruip et al. | 335/216 |
| 2011/0118588 A1* | 5/2011 | Komblau et al. | 600/411 |
| 2011/0156703 A1* | 6/2011 | O'Connor | 324/307 |
| 2011/0196226 A1* | 8/2011 | Gross et al. | 600/411 |
| 2011/0196227 A1* | 8/2011 | Gross et al. | 600/411 |
| 2011/0213239 A1* | 9/2011 | Amies et al. | 600/411 |
| 2011/0218420 A1* | 9/2011 | Carlone et al. | 600/411 |
| 2012/0150016 A1* | 6/2012 | Rathee et al. | 600/411 |
| 2014/0084926 A1* | 3/2014 | Amthor et al. | 324/309 |

FOREIGN PATENT DOCUMENTS

| | | |
|---|---|---|
| GB | 2 393 373 A | 3/2004 |
| JP | 10-57343 A | 3/1998 |
| WO | WO 02/065149 A1 | 8/2002 |
| WO | WO 2004/024235 A1 | 3/2004 |

OTHER PUBLICATIONS

International Search Report dated Sep. 26, 2006 (Thirteen (13) Pages).
Great Britain Search Report dated Sep. 27, 2005 (Two (2) Pages).
Form PCT/IPEA/416, and Form PCT/IPEA/409 (Eleven (11) Pages).
English Translation of Corresponding Japanese Office Action dated Nov. 9, 2010 (Four (4) pages).

* cited by examiner

PARTICLE RADIATION THERAPY EQUIPMENT

CROSS-REFERENCE TO RELATED APPLICATIONS

This application is related to co-pending U.S. patent application Ser. No. 11/917,940 filed concurrently herewith.

FIELD OF THE INVENTION

The present invention describes particle radiation therapy equipment which includes a magnet, thereby enabling magnetic resonance imaging (MRI) during particle radiation therapy.

BACKGROUND OF THE INVENTION

Radiation therapy with protons and carbon ion beams has been shown to be effective. In addition it has been shown to result in less damage to tissue than conventional gamma radiation therapy.

However, radiation planning for determining the magnitude and position of a dose to be administered is based on MRI imaging or CT imaging, which may have taken place at a considerable time period before the therapy takes place. In the intervening period, the position of the tissue to be irradiated may have moved, or changed shape. This may result in the irradiation of healthy tissue and/or missing diseased tissue, which may lead to a remission.

Figure 6:
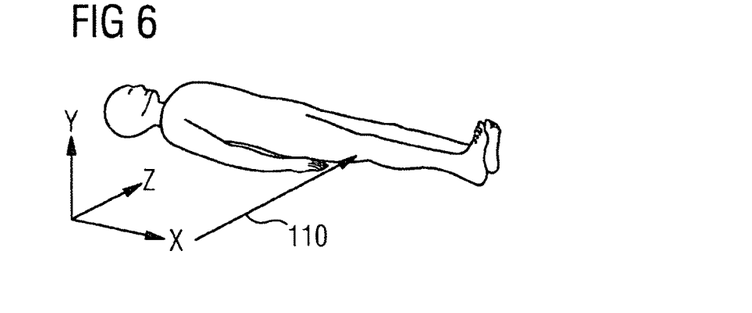
FIG. 6 shows an intended direction of application of a particle beam to a patient for performing particle radiation therapy.

In ion beam therapy, the patient is in general irradiated with a beam offered in a transverse direction 110 in transversal plane ZX, as schematically illustrated in FIG. 6.

It is desirable for the beam of charged particles to be applied to a patient at the same time as MRI imaging is taking place, since the position and shape of the intended target may then be accurately known in its current position.

The majority of present MRI scanners are not suitable for this because the beam would be obstructed by the cryostat. In addition, even in 'open' scanners such as those employing C- or H-shaped magnets, the magnetic field of the scanner will be perpendicular to the transverse direction 110 of the charged particle beam. This will deflect the beam from the intended direction.

Figure 7A:
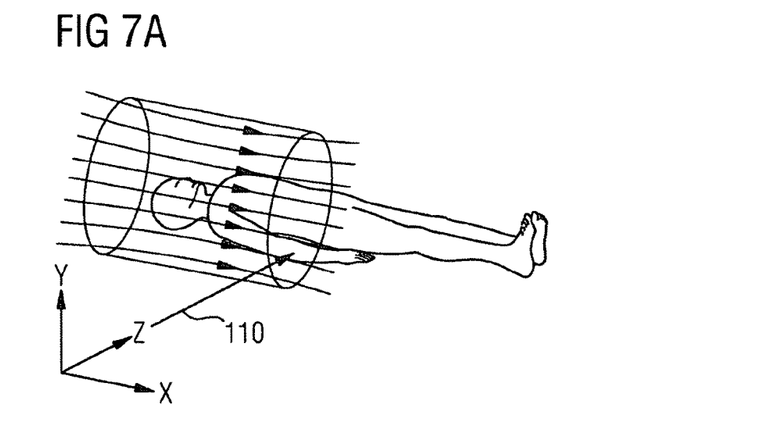
FIGS. 7A and 7B show magnetic fields generated by illustrated conventional MRI magnets with an intended direction of application of a particle beam for performing particle radiation therapy.
Figure 7B:
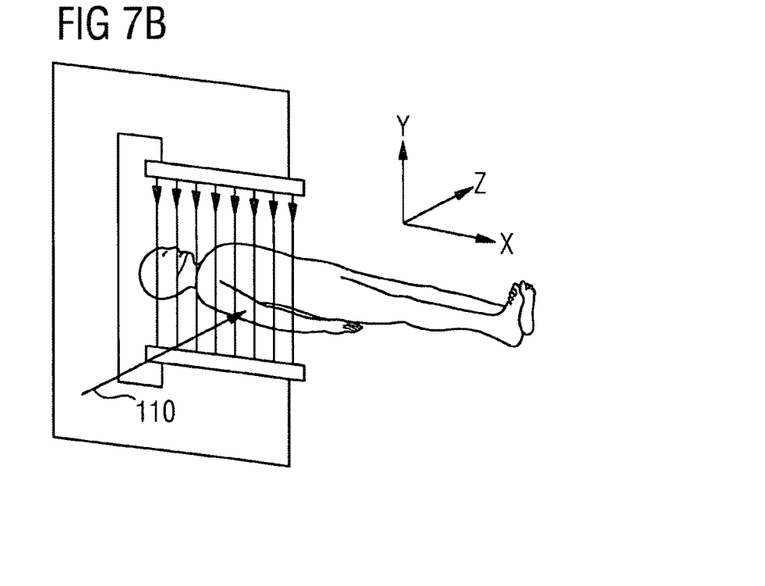

FIGS. 7A and 7B illustrate two examples of prior art MRI equipment, with the magnetic field B illustrated in terms of lines of magnetic flux. FIG. 7A shows a patient undergoing MRI imaging in a conventional solenoidal magnet arrangement. As illustrated, if it were possible to apply a beam of charged particles to the patient in the transverse direction 110 during MRI imaging, the beam would be perpendicular to the magnetic field B produced by the MRI equipment, and so the beam would be deflected from its intended target by the magnetic field B. In such a conventional solenoidal magnet arrangement, it is not possible to access the patient due to the presence of the solenoid surrounding the region of interest of the patient. FIG. 7B shows a patient undergoing MRI imaging in a conventional open C-shaped magnet arrangement. The patient is more accessible in such a magnet arrangement. However, as illustrated, if it were possible to apply a beam of charged particles to the patient in the transverse direction 110 during MRI scanning, the beam would be perpendicular to the magnetic field B produced by the MRI equipment, and so the beam would be deflected from its intended target by the magnetic field B.

WO02/065149 describes a coil arrangement for MRI systems, in which a transverse main magnetic field is generated. The coil arrangements described in that document produce a relatively large structure. Some of the described arrangements are difficult to manufacture. Certain embodiments of the present invention provide alternative arrangements for MRI systems, in which a transverse main magnetic field is generated, which are smaller overall structures and which employ coil arrangements which are simpler to manufacture.

US 2004/0199068 describes a system where MRI imaging is used to track the position of a target volume of a patient, and to gate the provision of a particle beam to a treatment volume, so that the particle beam is activated only when the treatment volume coincides with the target volume of the patient.

U.S. Pat. No. 6,198,957 describes a combined MRI imaging and particle beam treatment apparatus. The magnetic field of the MRI system is turned off while the particle beam treatment is applied.

According to the present invention, MRI imaging at the same time as particle radiation therapy is enabled by providing an MRI system which operates with a magnetic field in a transverse direction 110 parallel to the intended direction of application of the beam of charged particles, minimising the interference of the magnetic field with the charged particle beam while allowing access to the patient.

The present invention also provides methods for operating such equipment to perform particle radiation therapy at the same time as MRI imaging.

The present invention accordingly provides apparatus and methods as set out in the appended claims.

BRIEF DESCRIPTION OF THE FIGURES

For a better understanding of the invention and to show how the same may be carried into effect, there will now be described by way of examples only, specific embodiments, methods and processes according to the present invention with reference to the accompanying Figures, as shown in the accompanying drawing sheets, wherein.

DETAILED DESCRIPTION OF INVENTION

The present invention provides an application of a novel arrangement of magnet field coils to provide improved particle radiation therapy equipment. According to the present invention, a charged particle beam source is arranged to direct a charged particle beam in a predetermined direction to a region of application. Furthermore, magnetic field generation means are provided for generating a magnetic field in the region of application at the same time that the charged particle beam is applied, wherein the magnetic field generation means is arranged to provide access to the region of application for the charged particle beam, and to provide a homogeneous magnetic field in the region of application of the charged particle beam, said magnetic field being directed substantially in the predetermined direction.

Figure 1:
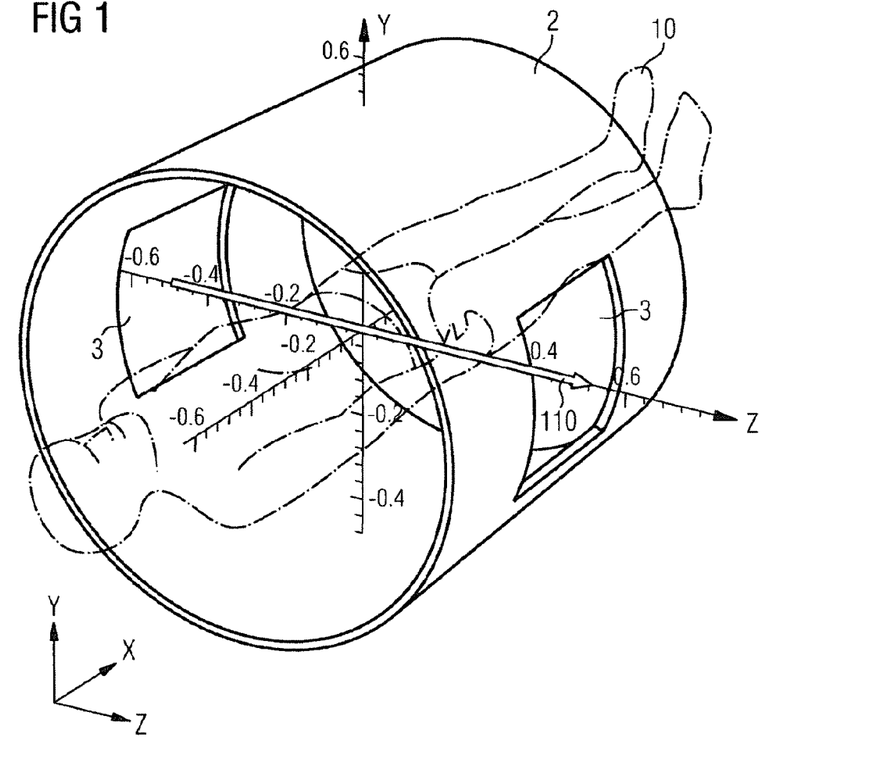
FIG. 1 shows a schematic overall view of the present invention, illustrating magnetic field generating equipment with access for particle radiation therapy.

A field magnet for generating a main magnetic field in an MRI system, according to an aspect of the present invention, is schematically shown in FIG. 1. The magnet consists of a cylindrical former 2, in which at least one opening 3 has been made. The former 2 may typically have an inside diameter of 1.0 m. The openings 3 shown in the FIG. are rectangular, but those skilled in the relevant art will appreciate that other shapes may also be suitable. A frame of axes XYZ is indicated. The X axis coincides with the axis of the cylindrical former 2. In operation, a patient 10 lies parallel to the X axis, as shown.

The field magnet itself consists of a number of conductors (not shown in FIG. 1) distributed as coils over the cylindrical former 2. In certain embodiments, it has been found preferable to arrange the current in the conductors such that it is distributed with reflective symmetry with respect to the XY plane. The current distribution is preferably also antisymmetric with respect to the ZX plane. The resultant magnetic field is directed in the transverse direction 110. In the illustrated arrangement, this is parallel to the Z axis.

The technology of winding complicated conductor shapes on to cylindrical formers has been developed for the manufacturing of magnets for circular high energy accelerators, such as dipoles, quadrupoles, and hexapoles, and methods of winding such conductor shapes will be familiar to those skilled in the art of manufacturing high field strength electromagnets.

In order to achieve a transverse main magnetic field in the direction 110 of sufficient strength and homogeneity for MRI imaging, the dimension and layout of coils on the cylindrical former 2 must be carefully planned.

Figure 2A:
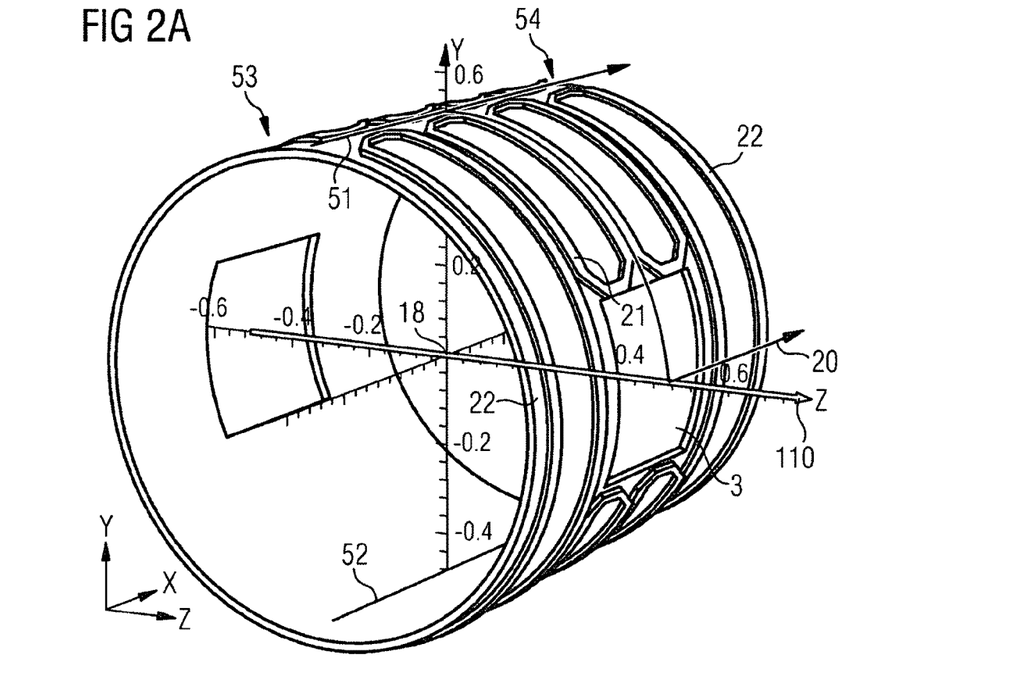
FIGS. 2A and 2B illustrate an example arrangement of magnet coils on a cylindrical former.

FIG. 2A shows one proposed layout of coils. In order to simplify the design and implementation of such a coil layout, a maximum of symmetry is imposed, such that the conductor patterns have reflective symmetry about XY, YZ and ZX planes. This in turn allows the coil layout to be planned in one octant 20 only.

Figure 2B:
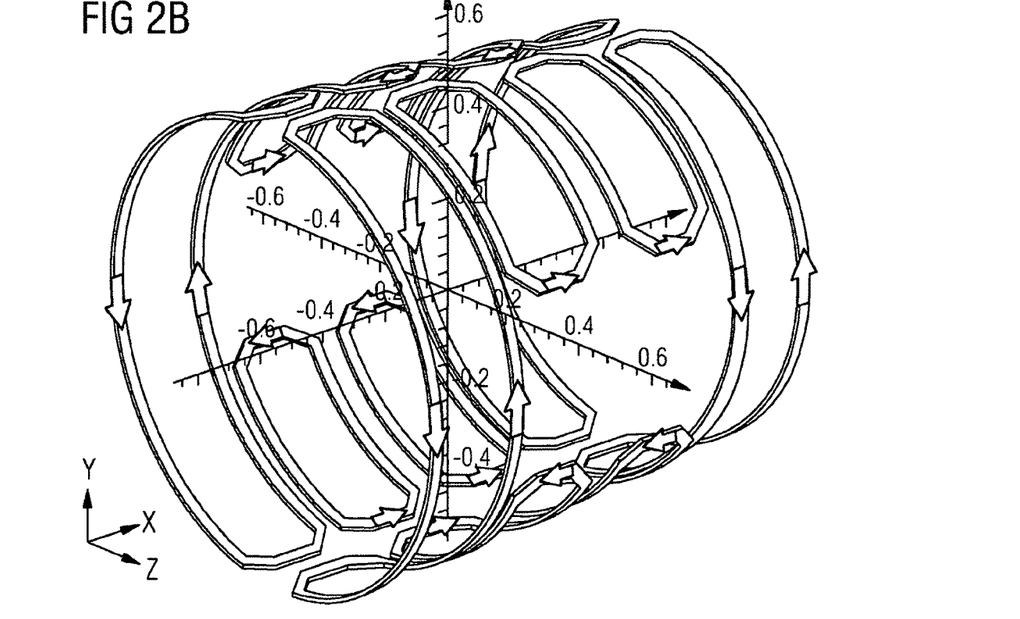

The octant 20 of the surface of the cylindrical former 2 is defined as one of the parts cut from the surface of the cylindrical former 2 when the surface is intersected by XY YZ and ZX planes each passing through the centre 18 of the cylindrical former. A coil layout is designed for one such octant 20, and is copied with appropriate symmetry onto the remainder of the surface of the cylindrical former 2. The coil layout preferably has symmetry in XY, YZ and ZX planes, such that the resulting current paths may be symmetrical about the XY plane, and antisymmetrical about the ZX plane. An example of suitable current directions is illustrated in FIG. 2B. As illustrated in FIG. 2A, of course, no conductors are allowed in that part of the former destined to become the openings 3. Coils such as 21 may be provided, which are contained entirely within one octant. Such coils would be placed in eight locations over the surface of the former. Coils such as 22 may be provided, which extend symmetrically about the ZX plane into two octants. Such coils would be placed in four locations over the surface of the former.

Figure 3:
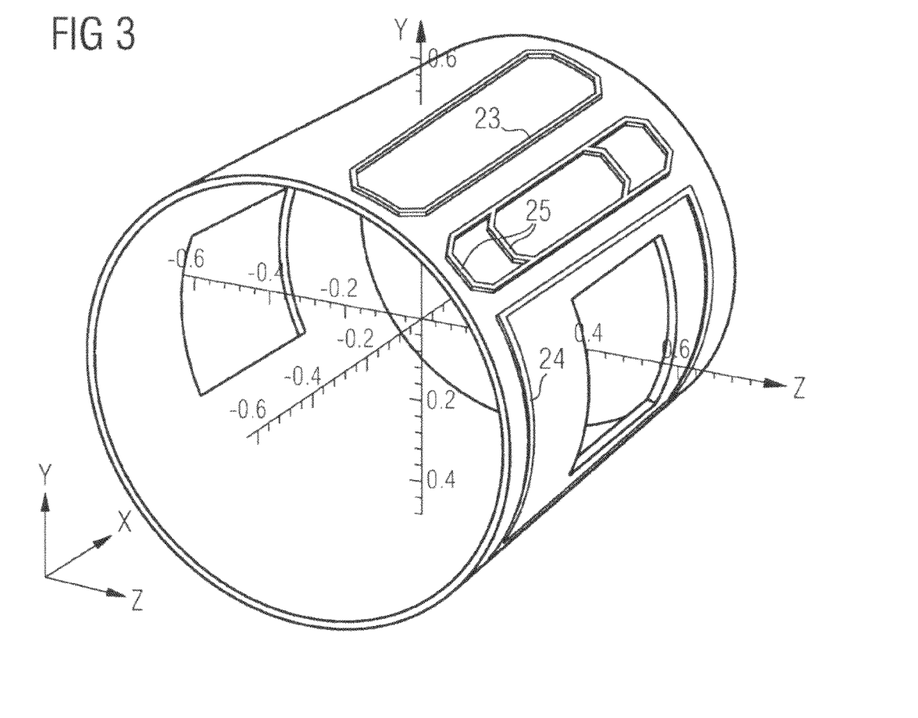
FIG. 3 illustrates another example arrangement of magnet coils on a cylindrical former.

FIG. 3 shows another possible layout of coils. As illustrated in FIG. 3, coils such as 23 may be provided, which extend into two octants symmetrically about the YZ plane. Such coils would also be placed in four locations over the surface of the former. Coils such as 24 may be provided, which extend into four octants symmetrically about the YZ and ZX planes. Such coils would be placed in two locations over the surface of the former. Overlapping coils such as 25 may be provided, wherein each coil is individually asymmetrically arranged, but the coils 25 are arranged in symmetrical, overlapping pairs. The coils need not all have the same cylindrical radius, so that multiple layers of coils may be lain over one another, to provide a required level of magnetic field strength and homogeneity in the complete arrangement.

One possible method for planning the layout of conductors on the cylindrical former 2 will be described with reference to FIG. 4. As described above, to simplify this process, an octal symmetry is assumed, such that the pattern of conductors will have symmetry in the XY, YZ and ZX planes. Then, by planning the conductor layout on one octant 20 of the surface of the cylindrical former 20, the appropriate symmetry may be applied to derive the conductor layout over the whole surface of the cylindrical former. Correspondingly, only one octant of the imaging volume sphere need be considered to calculate field strength and homogeneity over the whole imaging volume.

Typically, as in the present example, the imaging volume is assumed to be a sphere, centred at the centre 18 of the cylindrical former. In the present example, the imaging volume is assumed to be a sphere of radius 250 mm. One method of planning the conductor layout involves calculating a distribution of radial surface magnetisation of the cylindrical former, with a pair of openings 3, centred on the Z axis, cut out. The distribution of radial surface magnetism must be such the magnetic field in the imaging volume meets the required quality level. For example, the radial surface magnetism over the surface of the cylindrical former may be such that the RMS variation of the magnetic field strength on the surface of the imaging volume sphere is less than 5 ppm of the magnetic field strength at the centre of the imaging volume sphere.

A distribution of radial magnetisation on the available surface of the cylindrical former 2 may be found with help of a numerical optimiser. An example of a radial magnetisation distribution on one octant 20 of the former which achieves the required homogeneity level of the imaging volume mentioned above is shown in FIG. 4. Regions 41 have a high magnitude of magnetisation in a first radial direction, while regions 42 have a high magnitude of magnetisation in a second, opposite, radial direction.

Figure 4:
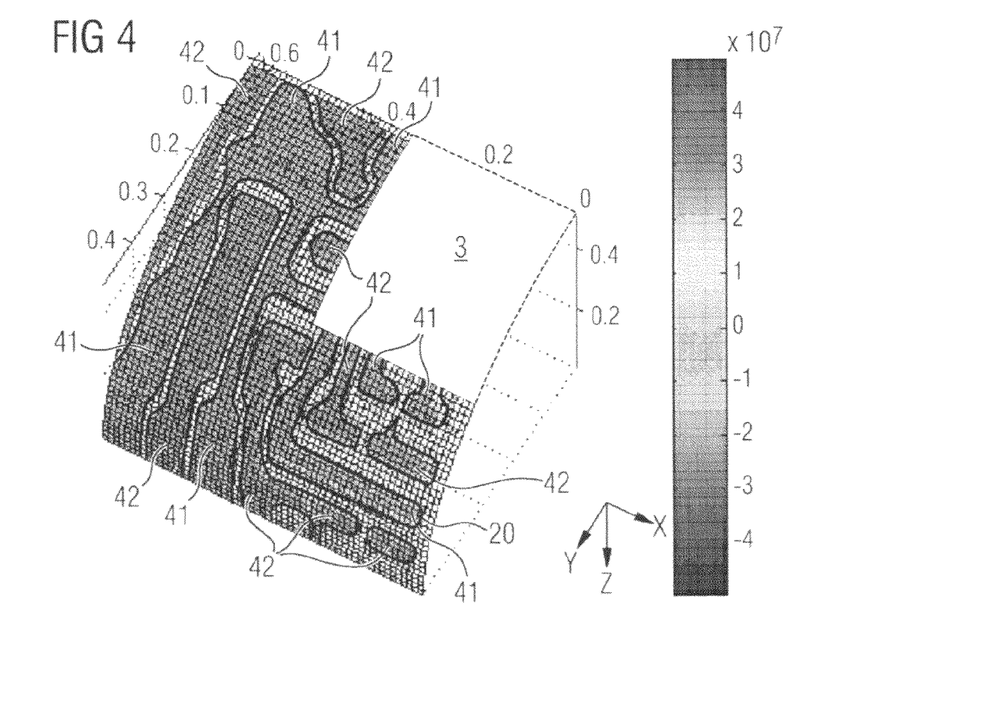
FIG. 4 shows a calculated optimal layout of surface radial magnetisation on one octant of the available surface of the cylindrical former.

Once the required radial surface magnetisation distribution on the available surface of the cylindrical former has been calculated, as illustrated in FIG. 4, then a conductor layout pattern must be derived, to indicate where conductors should be placed in order to produce the calculated radial surface magnetisation distribution, or a distribution acceptably close to it. This is done by first calculating a current distribution, which current distribution when applied to the available surface of the cylindrical former would produce the required radial surface magnetisation distribution.

Figure 5:
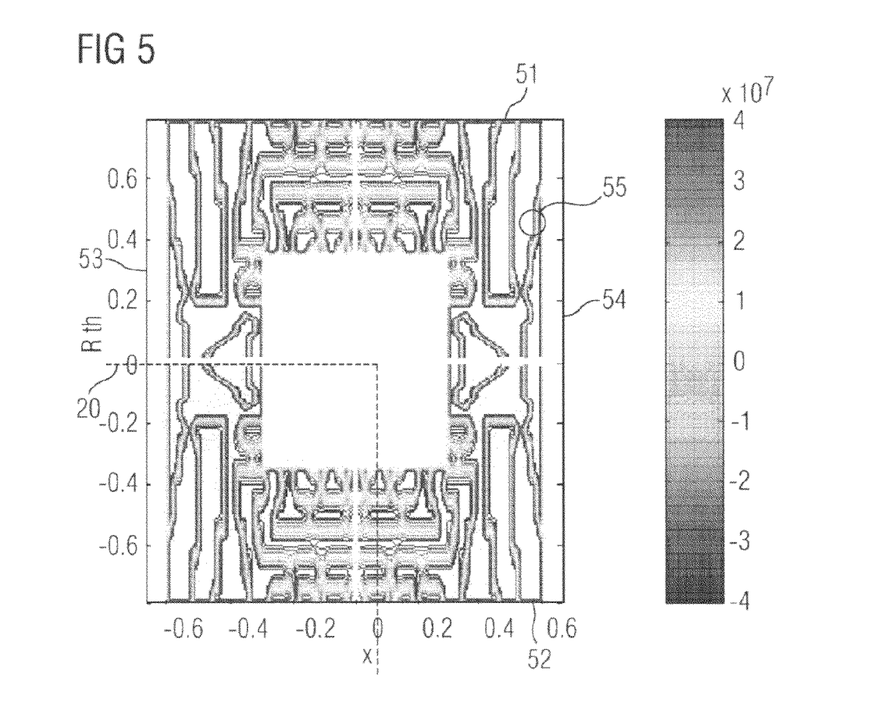
FIG. 5 shows a calculated optimal layout of current distribution over four octants of the available surface of the cylindrical former, derived from the calculated optimal layout of surface radial magnetisation of FIG. 4.

The current distribution may be calculated by finding the positions of closed contours of constant magnetisation in the calculated surface magnetisation distribution. A solution corresponding to the example of FIG. 4 is shown in FIG. 5, for the positive Z half of the cylindrical former, comprising four identical octants 20 arranged with the appropriate symmetry, being reflective symmetry about the YZ and ZX planes. The top edge 51 of the drawing of FIG. 5 corresponds to the top of the magnet (+Y) shown in FIG. 2. The bottom edge 52 of the drawing of FIG. 5 corresponds to the bottom of the magnet (−Y) shown in FIG. 2. The left and right sides 53, 54 correspond to the ends of the cylindrical former.

Although not clear from FIG. 5 itself, each line shown, such as at 55, has a contour of high positive magnetic field strength at one edge, and a contour of high negative magnetic field strength at the other edge, with the width of the line following a transition between these two levels. Such pattern of required magnetic field strength may be provided by a current flowing through a conductor, or a plurality of conductors, arranged along line 55. A number of current conductor paths may then be selected to closely replicate the lines of desired magnetic contours shown in FIG. 5. The coils chosen must respect the rules of symmetry which are required to produce the desired homogeneous transverse field. These rules are that the conductor paths must have reflective symmetry about XY, YZ and ZX planes, and that the current paths should have reflective symmetry about the XY plane, but should be antisymmetric about the ZX plane.

The pattern shown in FIG. 5, being derived from contours of radial magnetisation as shown in FIG. 4 may prove difficult to realise in practice. A level of engineering judgement must be exercised in order to identify a set of conductor windings which may be practically realised, and which will give an acceptable quality of main magnetic field in the imaging volume, in terms of magnetic field strength and homogeneity.

The present invention provides particle radiation therapy equipment, arranged to apply a charged particle beam to a region of application in a predetermined direction, further comprising a magnetic field generation means, arranged to generate a magnetic field in the region of application in the predetermined direction. Preferably, the magnetic field generation means comprises one of the coil arrangements discussed above.

The magnetic field generation means is preferably adapted for use in a magnetic resonance imaging system, such that magnetic resonance imaging of the region of application of the charged particle beam may be performed at the same time as the application of the charged particle beam.

The particle radiation therapy equipment preferably also comprises a cryostat unit and a gradient magnet assembly, wherein the said magnetic field generation means is situated within the cryostat whereby to provide an operating temperature at which superconductivity of the coils is possible, and wherein the gradient magnet assembly is operable to provide magnetic fields across predetermined planes whereby to enable magnetic resonance imaging.

The present invention also provides a method for performing particle radiation therapy on a patient at the same time as magnetic resonance imaging equipment on the patent. A charged particle beam is applied to a region of application in a predetermined direction. A homogeneous magnetic field is generated in the region of application of the charged particle beam, said magnetic field being directed substantially in the predetermined direction.

The magnetic field generation means may comprise a group of coils, each comprising windings of electrically conductive material; wherein the coils are arranged symmetrically about a midplane (XZ) and a plane of reflection (XY), the plane of reflection being perpendicular to the midplane, such that the coils have a plane of symmetry with respect to another plane (YZ), which is perpendicular to both the midplane and the plane of reflection, and wherein the windings are configured such that, in operation, current flow is symmetrical about the plane of reflection and anti-symmetrical about the midplane, to produce a resultant field at the centre of the group of magnet coils which is perpendicular to the plane of reflection (XY), and is directed substantially in the predetermined direction.

Preferably, the homogeneous magnetic field is generated by magnet coils arranged on a cylindrical former, where the predetermined direction is perpendicular to the axis of the cylindrical former. No coils should be present in an access region of the surface of the cylindrical former, said access region being centred on points of intersection of the predetermined direction with the surface of the cylindrical former. The coils may be arranged on an inner or an outer surface of the former, or may be embedded within the former.

The apparatus of the present invention may be arranged such that the former 2 and the charged particle source may rotate about the axis X, such that the particle beam, the magnetic field and the predetermined direction 110 may all approach the region of application, and so, in use, a patient, form a range of directions. This may be useful in applying particle radiation therapy to a certain region which is more accessible in one direction than in another.

The method may further comprise cooling the magnet coils to a temperature at which super conductivity is possible.

The currents may be applied to the magnet coils such that the direction of current flow is symmetrical about the plane of reflection (XY) and anti-symmetrical about the midplane (ZX).

While the present invention has been described with reference to a limited number of specific embodiments, by way of examples only, those skilled in the art will appreciate that numerous modifications and variations of the present invention may be derived within the scope of the appended claims.

References in the present document to particle radiation therapy or particle beam therapy, and similar terms, particularly include ion beam therapy and related concepts.

The embodiments described above employ cylindrical formers, that is, formers of uniform circular cross-section. However, the present invention may be applied to coils which are arranged on the surface of formers which are not cylindrical: formers which are tubular, but may not have a uniform cross-section, and whose cross-section may not be circular. The design and manufacture of such formers and coils is within the capability of those skilled in the art using currently available design tools.

The invention claimed is:

1. Particle radiation therapy equipment arranged to apply a charged particle beam in a predetermined direction (Z) to a region of application, said equipment comprising:
   a charged particle beam source arranged to direct a charged particle beam in the predetermined direction; and
   magnetic field generation means for generating a magnetic field in an imaging volume which includes the region of application, at the same time that the charged particle beam is applied; wherein
   the magnetic field generation means comprises coils that are arranged so as to provide access to the region of application for the charged particle beam, and to provide a homogeneous magnetic field in the region of application of the charged particle beam;
   said magnetic field is directed substantially in the predetermined direction;
   the coils are non-planar, and are arranged on a tubular former; and
   the predetermined direction is perpendicular to the axis of the tubular former.

2. The particle radiation therapy equipment according to claim 1, wherein:

the coils are arranged symmetrically about a midplane and a plane of reflection;

the plane of reflection is perpendicular to the midplane;

both the midplane and the plane of reflection extend in the direction of the axis of the former, such that the coils have a plane of symmetry with respect to another plane that is perpendicular to the axis of the former and both the midplane and the plane of reflection; and the coils are configured such that, in operation, current flow is symmetrical about the plane of reflection and anti-symmetrical about the midplane and the other plane, to produce a resultant field in the region of application which is perpendicular to the plane of reflection, and is directed substantially in the predetermined direction.

3. The particle radiation therapy equipment according to claim 1 wherein:

no coils are present in an access region of the tubular former; and said access region is centered on points of intersection of the predetermined direction with the tubular former.

4. The particle radiation therapy equipment according to claim 1, wherein the magnetic field generation means is adapted for use in a magnetic resonance imaging system.

5. The particle radiation therapy equipment according to claim 1, arranged such that the former and the charged particle beam source may rotate about the axis X of the former, such that the charged particle beam, the magnetic field and the predetermined direction may all approach the region of application from a range of directions.

6. The particle radiation therapy equipment according to claim 1, further comprising a cryostat unit and a gradient magnet assembly, wherein:

the magnetic field generation means is situated within the cryostat so as to provide an operating temperature at which superconductivity of the coils is possible; and the gradient magnet assembly is operable to provide magnetic fields across predetermined planes so as to enable magnetic resonance imaging.

7. A method for performing magnetic resonance imaging, said method comprising:

applying a charged particle beam in a predetermined direction to a region of application; and applying a homogeneous magnetic field in an imaging volume which includes the region of application of the charged particle beam; wherein, said magnetic field is directed substantially in the predetermined direction;

the homogeneous magnetic field is generated by non-planar coils arranged on a tubular former;

the predetermined direction is perpendicular to the axis of the tubular former; and the region of application does not include a living human or animal body or part thereof.

8. The method according to claim 7, wherein:

the magnet coils are arranged symmetrically about a midplane and a plane of reflection;

the plane of reflection is perpendicular to the midplanes;

both the midplane and the plane of reflection extend in the direction of the axis of the former, such that the coils have a plane of symmetry with respect to another plane, which is perpendicular to the axis of the former and both the midplane and the plane of reflections; and the coils are configured such that, in operation, current flow is symmetrical about the plane of reflection and anti-symmetrical about the midplane and the other plane, to produce a resultant field in the region of application which is perpendicular to the plane of reflection, and is directed substantially in the predetermined direction.

9. The method according to claim 7, further comprising:

cooling the magnet coils to a temperature at which super conductivity of the coils is possible; and causing electric current to flow in the coils.

10. The method according to claim 7. wherein:

no coils are present in an access region of the surface of the tubular former; and said access region is centered on points of intersection of the predetermined direction with the tubular former.

11. The equipment according to claim 1, arranged to perform ion beam therapy.

* * * * *